US012557799B1

(12) United States Patent
Diedrichsen

(10) Patent No.: US 12,557,799 B1
(45) Date of Patent: Feb. 24, 2026

(54) BREEDER DEVICE

(71) Applicant: Erik Joseph Diedrichsen, West Bridgewater, MA (US)

(72) Inventor: Erik Joseph Diedrichsen, West Bridgewater, MA (US)

( * ) Notice: Subject to any disclaimer, the term of this patent is extended or adjusted under 35 U.S.C. 154(b) by 0 days.

(21) Appl. No.: 19/189,205

(22) Filed: Apr. 24, 2025

(51) Int. Cl.
 *A01K 67/362* (2025.01)
 *A01K 39/014* (2006.01)
(52) U.S. Cl.
 CPC .......... *A01K 67/362* (2025.01); *A01K 39/014* (2013.01)
(58) Field of Classification Search
 CPC ............................ A01K 67/362; A01K 39/014
 See application file for complete search history.

(56) References Cited

U.S. PATENT DOCUMENTS

| | | | | |
|---|---|---|---|---|
| 11,533,896 B1 * | 12/2022 | White | ................... | A01M 1/106 |
| 2016/0157496 A1 * | 6/2016 | Nchekwube | ........ | A01M 1/2016 |
| | | | | 424/84 |
| 2019/0177046 A1 * | 6/2019 | Hoff | ....................... | A01G 29/00 |
| 2019/0216075 A1 * | 7/2019 | McGavin | .............. | A01M 1/106 |

FOREIGN PATENT DOCUMENTS

| | | | | | |
|---|---|---|---|---|---|
| CA | 2214612 A1 | * | 5/1998 | ............. | A01K 31/14 |
| CN | 118525772 A | * | 8/2024 | ............. | B08B 9/087 |
| KR | 20150031867 A | * | 3/2015 | ........... | A01K 39/014 |

OTHER PUBLICATIONS

Morelia Australia (Year: 2020).*
Acorn Land (Year: 2023).*
BSF Composting Guide, Purdue University (Year: 2022).*
Black Soldier Fly (Year: 2010).*
Garden Pool (Year: 2011).*

* cited by examiner

*Primary Examiner* — Monica L Perry
*Assistant Examiner* — Aaron M Rodziwicz
(74) *Attorney, Agent, or Firm* — Wilson Dutra, PLLC; Camille A. Wilson

(57) ABSTRACT

The present disclosure provides a breeder device with a lid-like body, wherein the breeder device includes a lip attachable to a breeding container. In some embodiments, the breeder device may include a breeder device access point, at least one aperture, a tray, and one or more stabilizing legs. In some aspects, breeding material may be added to a breeding container, wherein the breeder device may be configured to promote the reproduction of flies to produce larvae that may be fed to farm animals.

20 Claims, 10 Drawing Sheets

200

235

250

255

225 240

245

230

210

220

BREEDER DEVICE

BACKGROUND

Fly larvae provide an efficient and effective means for converting organic waste into high-quality fertilizer. Specifically, these larvae consume food waste and animal manure, wherein the larvae's digestive system breaks down the food waste and animal manure and excrete it as nutrient-rich residue called frass. The benefits of fly larvae are two-fold as the frass may be used as fertilizer and the larvae may provide a food source for farm animals.

Currently, there are a number of devices designed to breed flies to produce larvae that may break down waste to create fertilizer while also creating a supply of larvae to feed to animals. Unfortunately, these devices face a number of difficulties that may result in poor performance, expensive products, difficulty in maintenance, and overcrowding. M any of these issues are a result of complex designs that require intricate design functionality.

For example, many of these breeder devices accumulate odors, mold, and contaminants that may degrade conditions of the breeder devices such that they no longer function well or at all. To prevent the accumulation of these odors, mold, and contaminants, breeder devices must be cleaned frequently and maintained to promote adequate production of larvae. With their complexity in design, these cleaning processes may require the taking apart or breaking down of the breeder devices.

There is an opportunity to improve the current devices for breeding fly larvae. A device that is simple and effective may provide a more practical solution for farmers. This may allow farmers to breed larvae that may improve their crop production while serving as a source of feed for farm animals. If these devices included simple components that may be easily accessed, cleaned, and replaced, they may lead to breeder devices being far more commonplace in farming environments.

SUMMARY OF THE DISCLOSURE

What is needed is a breeder device that promotes the growth of larvae effectively and efficiently. In some embodiments, the breeder device may include a lid configured to attach to a breeding container, wherein the lid includes a lip.

In some implementations, the breeder device may include a door connected to the lid. In some aspects, the breeder device may include a breeder device access point protruding from both sides of the door, wherein the breeder device access point may include an internal cavity accessible from each side of the breeder device. In some implementations, the breeder device may include at least one or more stabilizing legs attached to the curved edge of the breeder device.

A number of embodiments of the present disclosure will be described. While this specification contains many specific implementation details, these should not be construed as limitations on the scope of any disclosures or of what may be claimed, but rather as descriptions of features specific to particular embodiments of the present disclosure. It is understood to those skilled in the art that variations, modifications, and alterations may be apparent. It will be understood that various modifications may be made without departing from the spirit and scope of the disclosure.

BRIEF DESCRIPTION OF THE DRAWINGS

The accompanying drawings that are incorporated in and constitute a part of this specification illustrate several embodiments of the disclosure and, together with the description, serve to explain the principles of the disclosure.

DETAILED DESCRIPTION

The present disclosure provides generally for a breeder device configured to facilitate the production of larvae for high quality fertilizer and for farm animal feed. According to the present disclosure, the breeder device may include a breeder device access point, a door, a tray, and one or more stabilizing legs.

In the following sections, detailed descriptions of examples and methods of the disclosure will be given. The description of both preferred and alternative examples, though thorough, are exemplary only, and it is understood to those skilled in the art that variations, modifications, and alterations may be apparent. It is therefore to be understood that the examples do not limit the broadness of the aspects of the underlying disclosure as defined by the claims.

Glossary

Breeder device: as used herein refers to a device attachable to a breeding container, wherein the breeder container may contain breeding material. In some aspects, the breeder device may include a lid for the breeding container, wherein the breeder device includes a door, a breeder device access point, a tray, at least one aperture, and one or more stabilizing legs. In some implementations, the breeder device may be configured to receive flies, wherein the flies may access the breeding material in the breeding container, wherein the flies may breed larvae that may be captured on the tray to be fed to farm animals like poultry, as a non-limiting example.

Breeder device access point: as used herein refers to a portion of the breeder device configured provide a pathway through the breeder device. In some aspects, the breeder device access point may include an internal cavity accessible through a first opening and a second opening. In some implementations, the breeder device access point may be included on a door on the breeder device.

Figure 1:
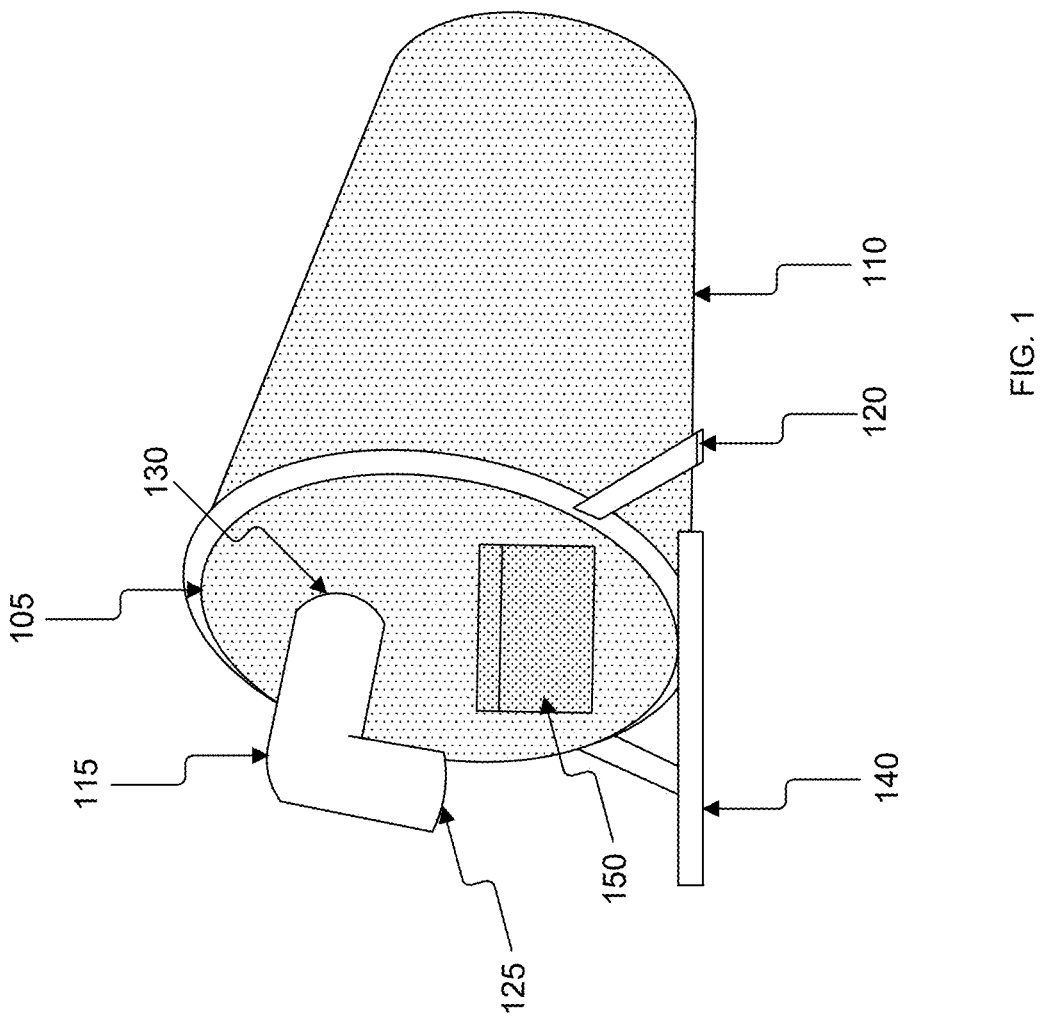
FIG. 1 illustrates a breeder device connected to a breeding container, according to some embodiments of the present disclosure.

Referring now to FIG. 1, a breeder device connected to a breeding container, according to some embodiments of the present disclosure, is illustrated. In some embodiments, the breeder device 105 may include a lid-like body which may be configured to be attachable to a breeding container 110, wherein the lid-like body may include a lip that may surround a circular center. In some aspects, the breeder device 105 may include a breeder device access point 115. In some implementations, the breeder device 105 may include a door 135 connected to the lid, wherein the door 135 opens and closes to provide access to breeding container 110.

In some implementations, the breeder device 105 may include a breeder device access point 115 to the lid. In some embodiments, a breeder device access point 115 may protrude from both sides of the door 135, wherein the breeder device access point 115 may include an internal cavity accessible from each side of the breeder device 105. By way of example and not limitation, the breeder device access point 115 may include rubber, plastic, metal, and silicone.

In some implementations, the breeder device 105 may include one or more stabilizing legs 120 extending from the curved edge. In some aspects, the breeder device access point 115 may be L-shaped, wherein one side of the breeder device access point 115 may include an angle, wherein an end of the breeder device access point 115 may include a first opening 125. In some implementations, the side of the breeder device access point 115 opposite of the L-shaped portion may include a second opening 130.

In some embodiments, the breeder device 105 may be configured to connect to the breeding container 110. By way of example and not limitation, the breeding container 110 may include a bucket, a trough, a bin, or a barrel. In some aspects, the breeding container 110 may include a 5-gallon bucket, as a non-limiting example. In some aspects, the breeder device 105 may be configured to connect to the breeding container 110, wherein the breeder device 105 may secure itself with the breeding container 110. By way of example and not limitation, the breeder device 105 may include a lid, wherein the breeding container 110 may include a bucket, wherein the breeder device 105 may be configured as the lid for the bucket.

In some implementations, the door 135 may be attached to the lid through a hinge or lever mechanism, wherein the door 135 may open and close. In some aspects, the opening of the door 135 may allow breeding material to be placed into the breeding container 110 or may allow for the cleaning of the breeding container 110, as non-limiting examples. In some aspects, the first opening 125 of the breeder device access point 115 may protrude outside of the breeding container 110, wherein the second opening 130 of the breeder device access point may protrude into the breeding container 110. In some aspects, the one or more stabilizing legs 120 may be positioned to stabilize or elevate the breeder device 105 and the connected breeding container 110, as non-limiting examples.

By way of example and not limitation, the breeding container 110 may be configured to contain breeding material. In some aspects, the breeding material may be configured to draw flies or other insects into the breeding container 110 through the breeder device access point 115, wherein the flies or other insects may consume the breeding material. In some embodiments, the flies or other insects may convert the breeding material into fertilizer, as non-limiting examples. In some aspects, the flies or other insects may breed on the breeder device 105 or inside the breeding container 110, wherein the flies or other insects produce larvae. In some aspects, the larvae may be provided as feed for farm animals, as a non-limiting example. In some implementations, the breeder device 105 may include a tray 140 configured to catch any larvae that may exit the breeder device through the breeder device access point 115.

Figure 2:
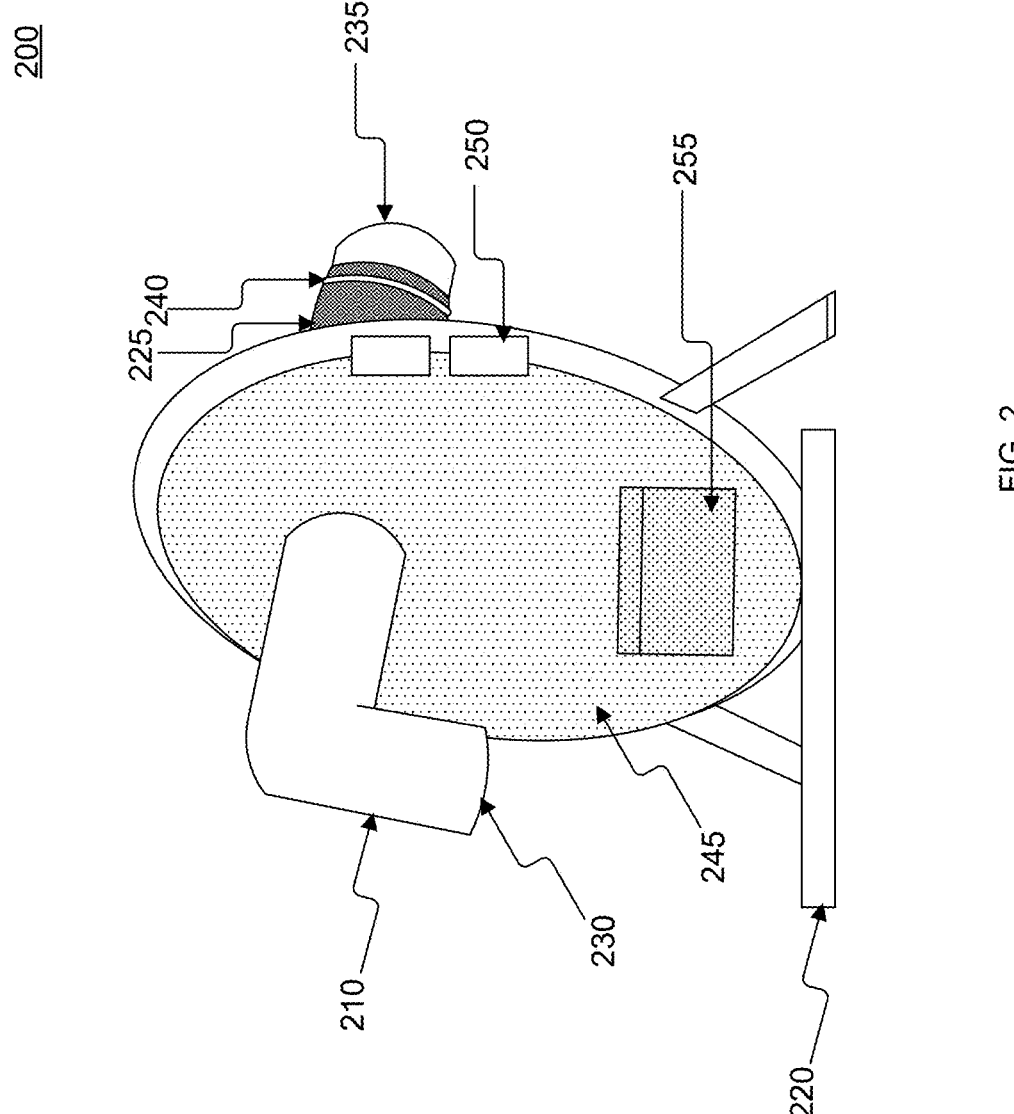
FIG. 2 illustrates a breeder device, according to some embodiments of the present disclosure.

In some embodiments, the breeder device 105 may include at least one aperture 150, wherein the at least one aperture may Referring now to FIG. 2, a breeder device, according to some embodiments of the present disclosure, is illustrated. In some aspects, the breeder device 200 may include a breeder device access point 210, one or more stabilizing legs 215, at least one aperture 255 a tray 220, and a breeding platform 225. In some embodiments, the breeder device access point 210 may include a front end with a first opening 230 and a back end with a second opening 235.

In some aspects, the back end of the breeder device 200 may include the breeding platform 225. In some implementations, the breeding platform 225 may be attached to the back end of the breeder device 200 through a securing mechanism 240. By way of example, the securing mechanism 240 may be rubber bands, strings, rope, adhesives, pins, or screws. In some aspects, the breeding platform 225 may include cardboard or plastic. In some aspects, the breeding platform 225 may be configured to receive eggs from a fly or insect. In some implementations, the breeder device 200 may include a door 245 that may be opened or closed along hinges 240 that 5 may be configured to connect the door 245 to the breeder device 200.

Figure 3:
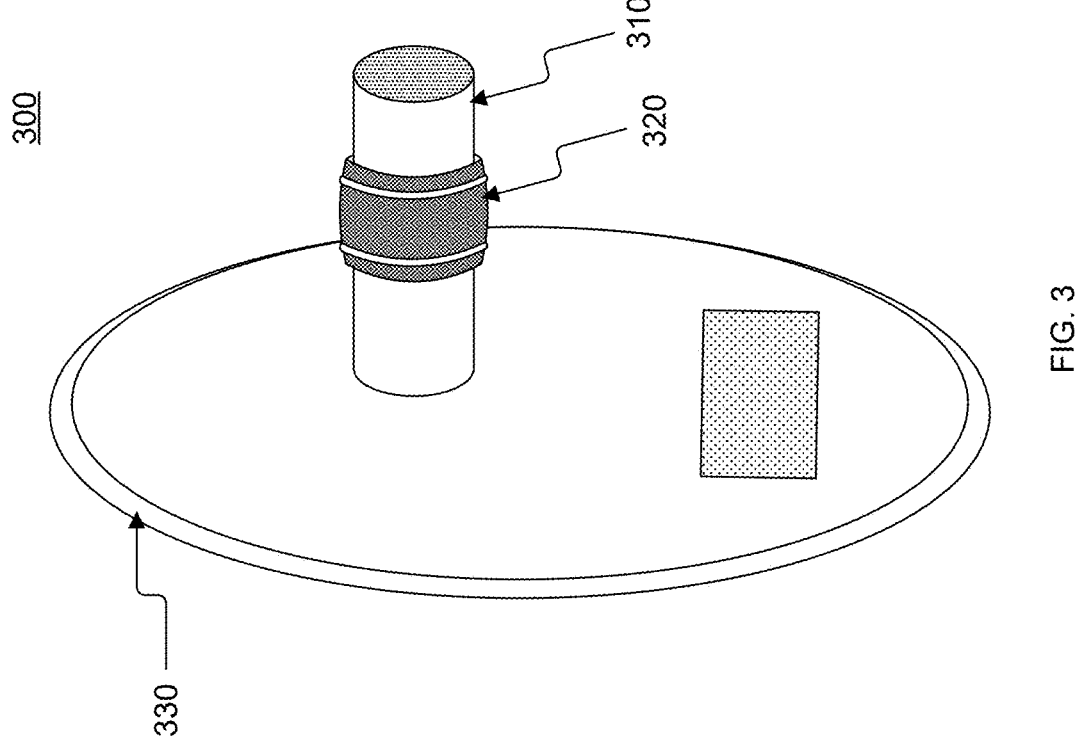
FIG. 3 illustrates a perspective of the back end of a breeder device, according to some embodiments of the present disclosure.

Referring now to FIG. 3, a perspective of the back end of a breeder device, according to some embodiments of the present disclosure, is illustrated. In some aspects, the breeder device 300 may include a breeder device access point 310, a breeding platform 320, and an attachment mechanism 330. In some implementations, the attachment mechanism 330 may be included on a lip of the breeder device 300, wherein the attachment mechanism 330 may be configured to snap into, latch onto, or adhere, as non-limiting examples, to a breeding container.

In some embodiments, the breeder device access point 310 may include a breeding platform 320 configured to induce the breeding of flies and other insects. In some aspects, the flies and other insects may produce larvae that may be used to feed farm animals. In some implementations, the breeder device 300 may connect to the breeding container which contains breeding material that may be converted into fertilizer for the flies and other insects. In some aspects, the breeding material may be eaten by the flies and other insects.

Figure 4:
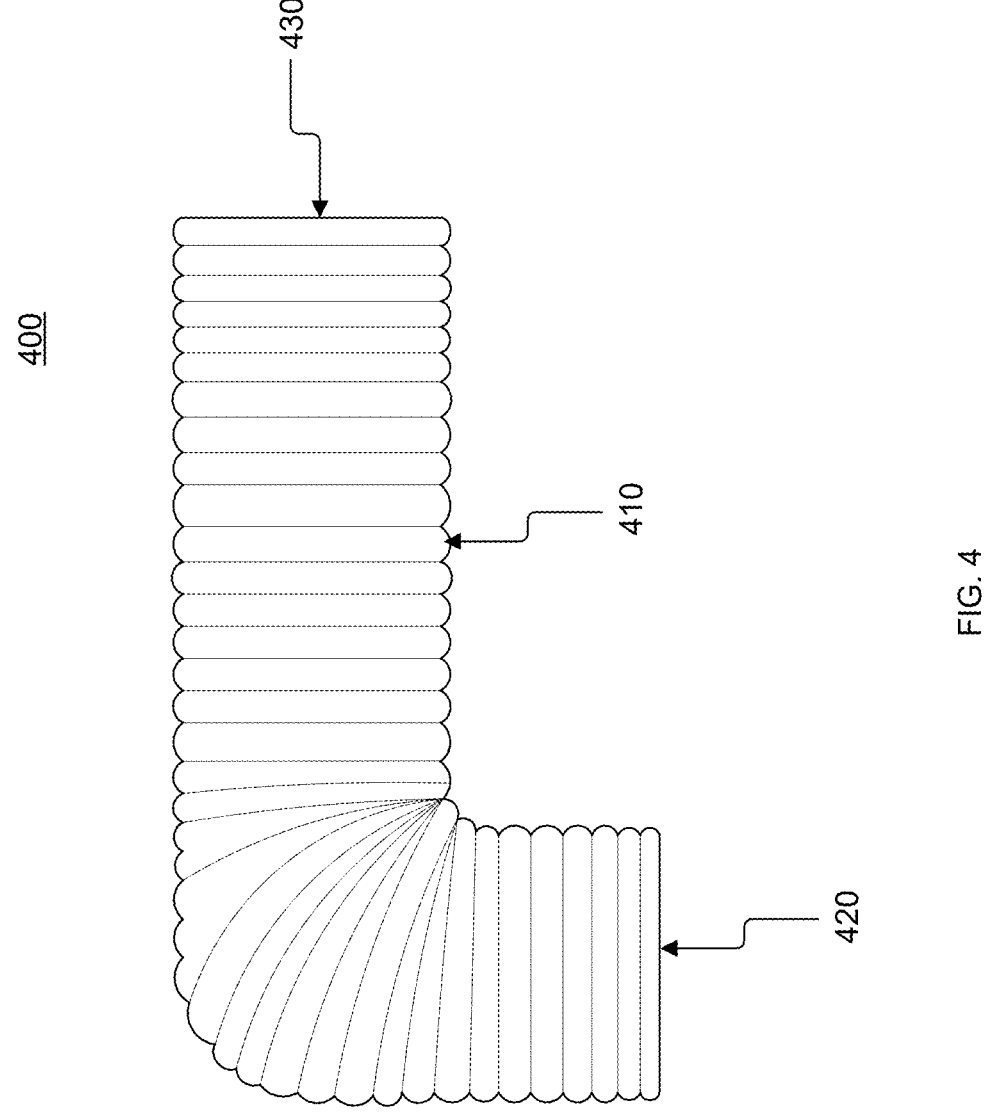
FIG. 4 illustrates a breeder device access point, according to some embodiments of the present disclosure, is illustrated.

Referring now to FIG. 4, a breeder device access point, according to some embodiments of the present disclosure, is illustrated. In some aspects, the breeder device access point 400 may include a substantially rigid material. In some embodiments, the breeder device access point 400 may include rubber, plastic, metal, and silicone, as non-limiting examples. In some aspects, the breeder device access point 400 may include a plurality of bellows 410 configured to allow mobility of the breeder device access point 400.

In some implementations, the breeder device access point 400 may include a front side with a first opening 420 and a back side with a second opening 430, wherein the breeder device access point 400 may include an internal cavity. In some aspects, the breeder device access point 400 may provide a tunnel for flies or other insects to enter a breeding container. In some aspects, the plurality of bellows 410 may enable the breeder device access point 400 from being positioned where flies and other insects may enter the breeder device access point 400.

Figure 5:
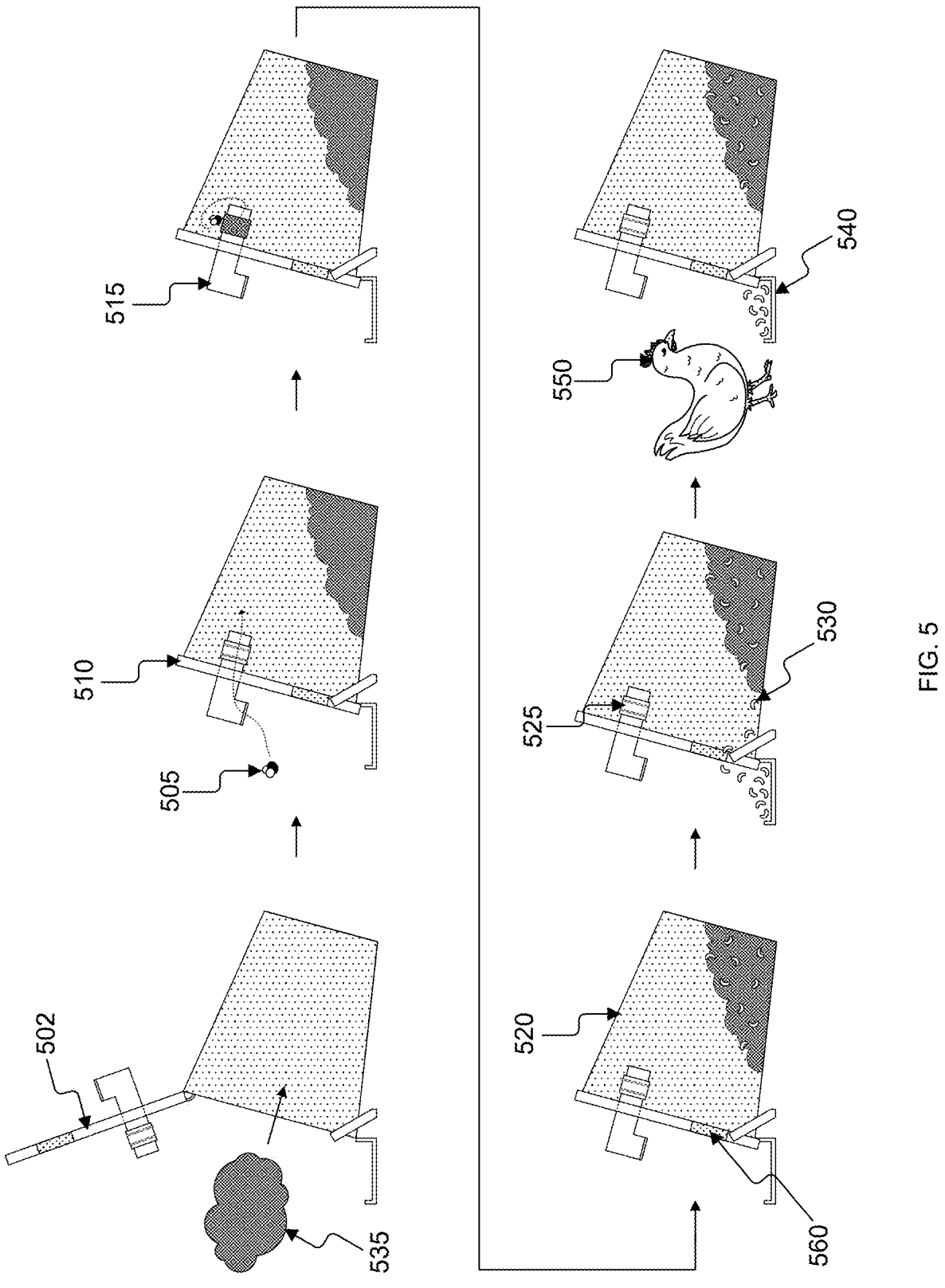
FIG. 5 illustrates a process flow for a breeder device, according to some embodiments of the present disclosure.

Referring now to FIG. 5, a process flow for a breeder device, according to some embodiments of the present disclosure, is illustrated. In some embodiments, door 502 on a breeder vessel 510 may be opened to provide access to a breeding container 520, wherein breeding material 535 may be added to the breeding container 520. In some embodiments, a fly 505 may enter the breeding vessel 510 through a breeding vessel portal 515 that protrudes into the breeding container 520. In some implementations, the fly 505 may be drawn to a breeding platform 525, wherein the fly 505 may lay eggs on the breeding platform 525. In some aspects, the eggs may hatch into larvae 530.

In some embodiments, the larvae 530 may move through the breeding container 520 to feed on the breeding material 535. In some aspects, the larvae 530 may consume the breeding material 535, wherein the breeding material 535 may include organic material, wherein the larvae 530 may convert it into fertilizer. In some implementations, the larvae 530 may leave the breeding container 520, wherein the larvae 530 may be captured by a tray 540. In some embodiments, a farm animal 550 may eat the larvae 530 on the tray 540, wherein the larvae 530 may provide nutrients and food to the farm animal 550. By way of example and not limitation, the farm animal 550 may be poultry. By way of example and not limitation, breeding material may include compost, waste, soil, or organic material.

Figure 6:
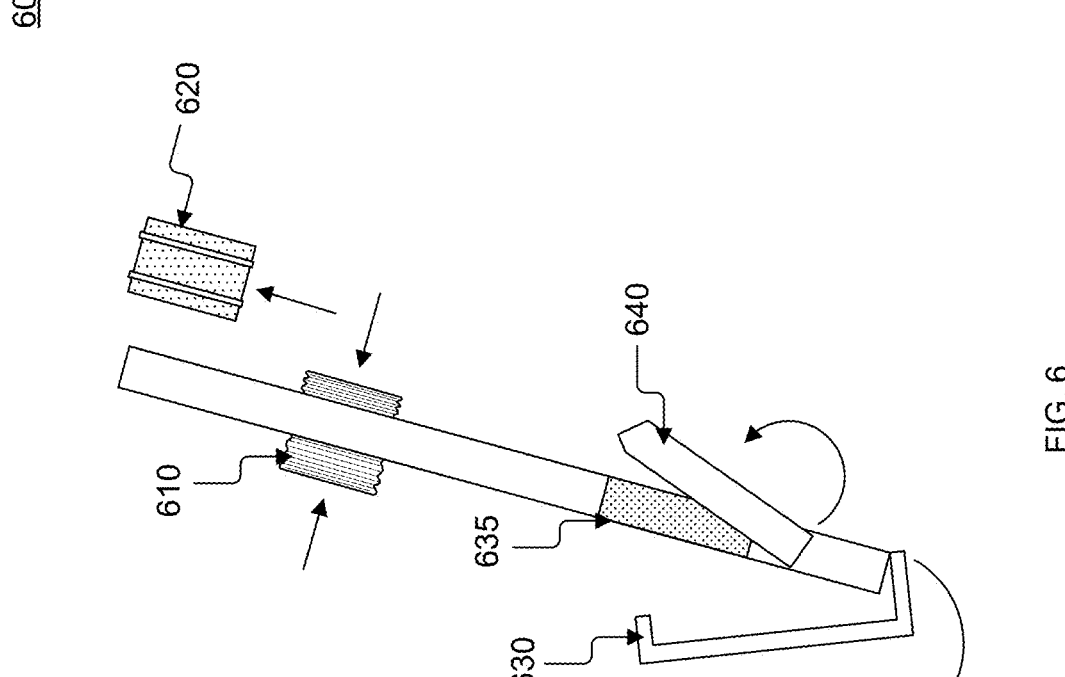
FIG. 6 illustrates a side view of a breeder device, according to some embodiments of the present disclosure.

Referring now to FIG. 6, a side view of a breeder device, according to some embodiments of the present disclosure, is illustrated. In some embodiments, the breeder device 600 may include a breeder device access point 610, a breeding platform 620, a tray 630, at least one aperture 635, and one or more stabilizing legs 640. In some implementations, the breeder device access point 610 may be collapsable and capable of movement, wherein the breeder device access point 610 may include one or more bellows that may fold inward to reduce the size of the breeder device access point 610.

In some embodiments, the breeding platform 620 may be attachable to the breeder device access point 610, wherein the extended breeder device access point 610 may receive the breeding platform 620. In some implementations, the tray 630 may be configured to fold inwards and outwards, wherein the folding the tray 630 outwards may configure the tray 630 to receive larvae from a breeding container. In some aspects, the one or more stabilizing legs 640 may be configured to fold inwards and outwards, wherein the one or more stabilizing legs 640 may be adjustable to stabilize and position the breeder device 600. In some aspects, the tray 630 and the one or more stabilizing legs 640 may include hinges, wherein the hinges allow for the movement of the tray 630 and the one or more stabilizing legs 640.

Figure 7:
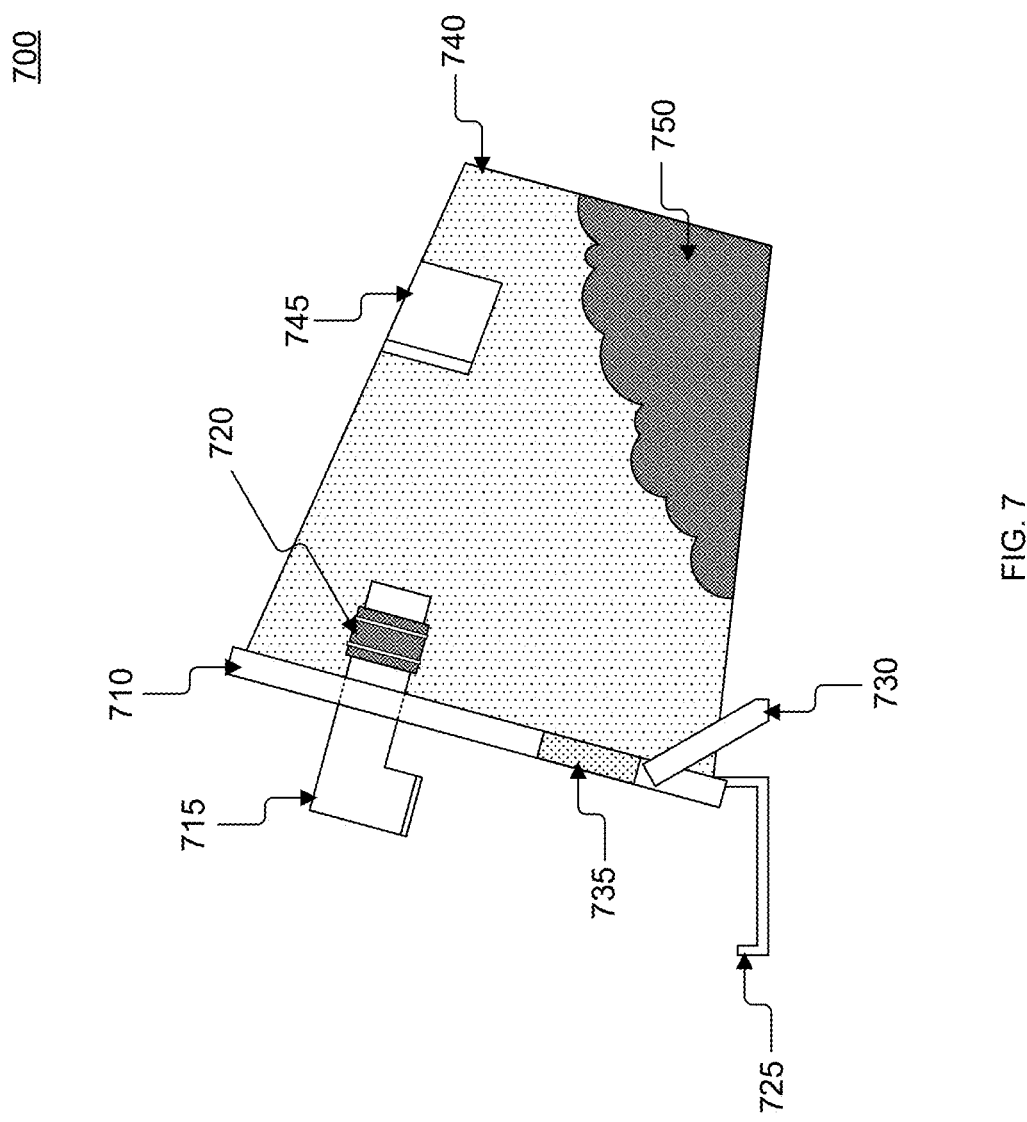
FIG. 7 illustrates a breeder device connected to a breeding container, according to some embodiments of the present disclosure.

Referring now to FIG. 7, a breeder device connected to a breeding container, according to some embodiments of the present disclosure, is illustrated. In some embodiments, the breeding vessel 710 may include a breeder device access point 715, a breeding platform 720, a tray 725, one or more stabilizing legs 730, and at least one aperture 735. In some implementations, the breeder device 710 may be connected to a breeding container 740. In some aspects, the breeding container 740 may be a trough, bin, or bucket, as non-limiting examples.

In some embodiments, the breeding container 740 may be the bucket, wherein the bucket includes at least one opening 745 on its side closest to its base. In some implementations, breeding material 750 may be received by the at least one opening 745. In some aspects, the at least one opening 745 may include a door configured to open and close. In some embodiments, the breeding material 750 may provide food for the flies, larvae, and other insects, wherein the flies, larvae, and other insects may convert the breeding material into fertilizer, as non-limiting examples.

Figure 8:
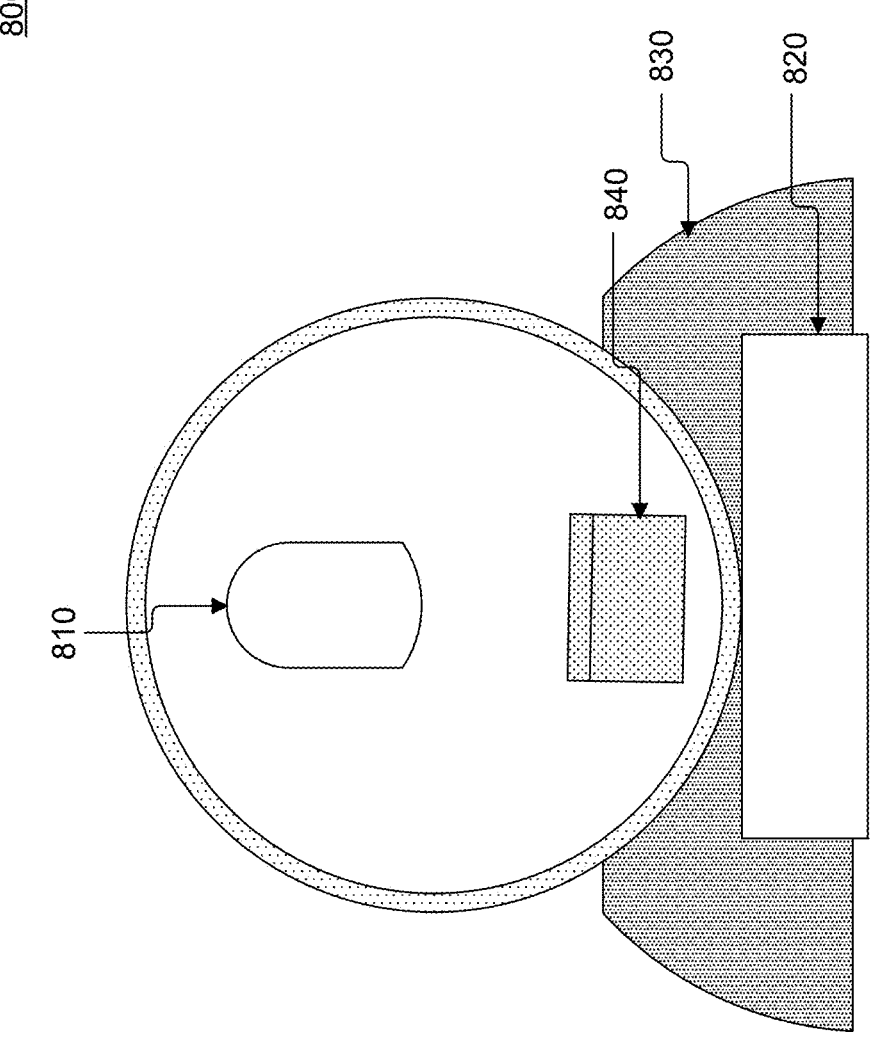
FIG. 8 illustrates a front view of the breeder device connected to a breeding container, according to some embodiments of the present disclosure.

Referring now to FIG. 8, a front view of the breeder device connected to a breeding container, according to some embodiments of the present disclosure, is illustrated. In some embodiments, the breeder device 800 may include a breeder device access point 810 and a tray 820. In some embodiments, the tray 820 may be connected to a bottom edge of the breeder device 800, wherein the tray may include a curved lip configured to match the shape of the bottom edge of the breeder device 800. In some implementations, the tray 820 may be configured as the stabilizing legs 830 of the breeder device 800, wherein the tray 820 protrudes from the breeder device 800 and may be configured to provide a flat surface to receive larvae that may exit the breeder device 800 from a breeding container through the breeder device access point 810. In some aspects, the bottom of the tray 820 may rest against a floor or the ground to stabilize the breeder device 800. In some embodiments, the breeder device 800 may include at least one aperture 840 configured to provide a pathway for larvae to leave the breeding container.

Figure 9:
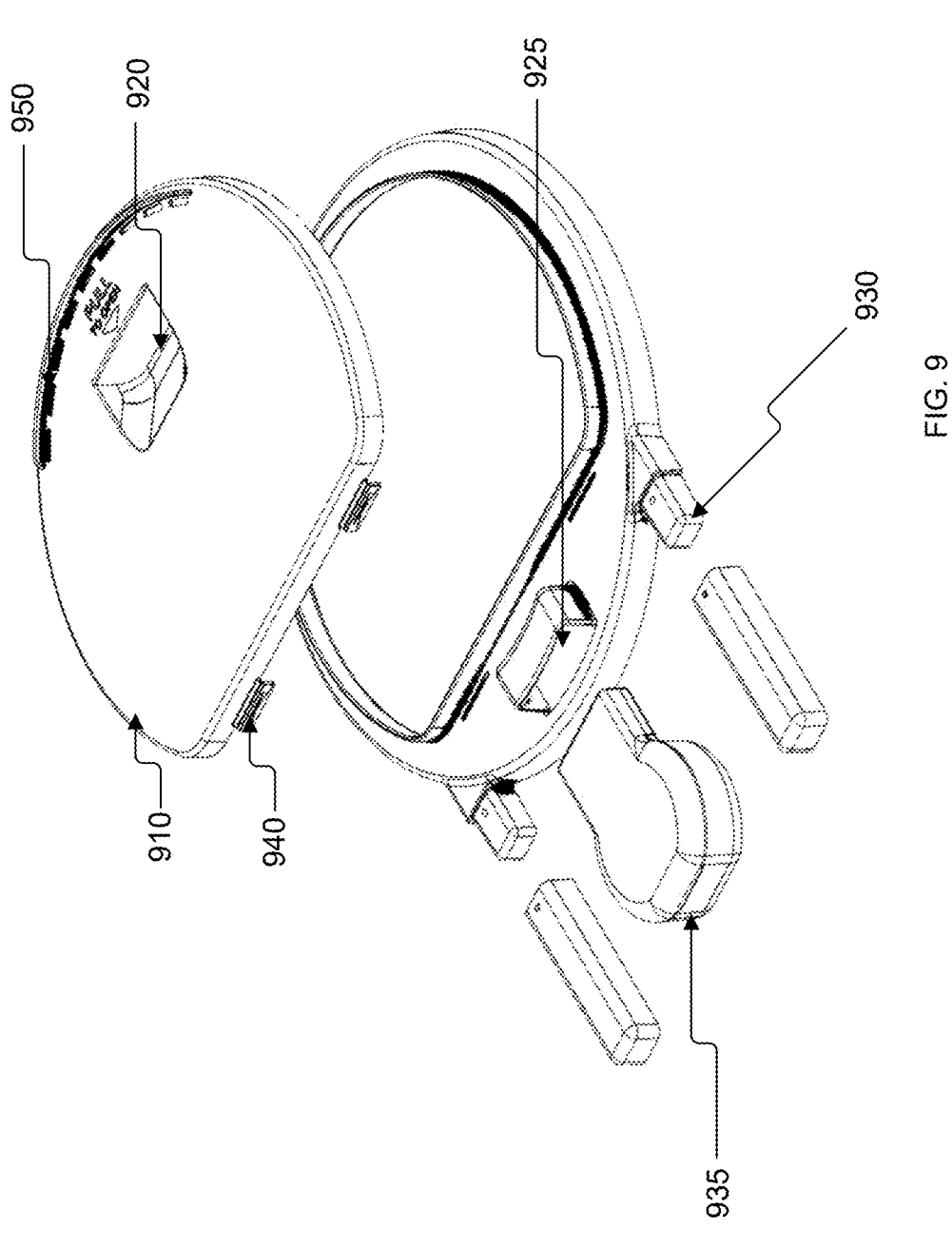
FIG. 9 illustrates a breeder device, according to some embodiments of the present disclosure.

Referring now to FIG. 9, a breeder device, according to some embodiments of the present disclosure, is illustrated. In some embodiments, the breeder device 900 may include a door 910, a breeder device access point 920, and an attachment mechanism 930. In some implementations, the door 910 may include one or more hinges 940, wherein the door 910 may be configured to open and close at the one or more hinges 940. In some aspects, the breeder device 900 may be connectable to a breeding container, wherein the opening of the door 910 may provide access into the breeding container.

In some implementations, the breeder device 900 may include at least one aperture configured to provide a pathway for larvae to leave the breeding container and a tray 935 configured to catch or receive the larvae, as non-limiting examples, wherein one or more farm animals may consume the larvae from the tray as food. In some aspects, the breeder device 900 may include a handle configured to provide leverage to open and close the door 910. In some implementations, the attachment mechanism 930 may be configured to secure the breeder device 900 to a breeding container. In some embodiments, the breeder device 900 may include one or more holes 950 configured to provide another point of access for flies and to provide some breathability to the breeder device 900.

Figure 10:
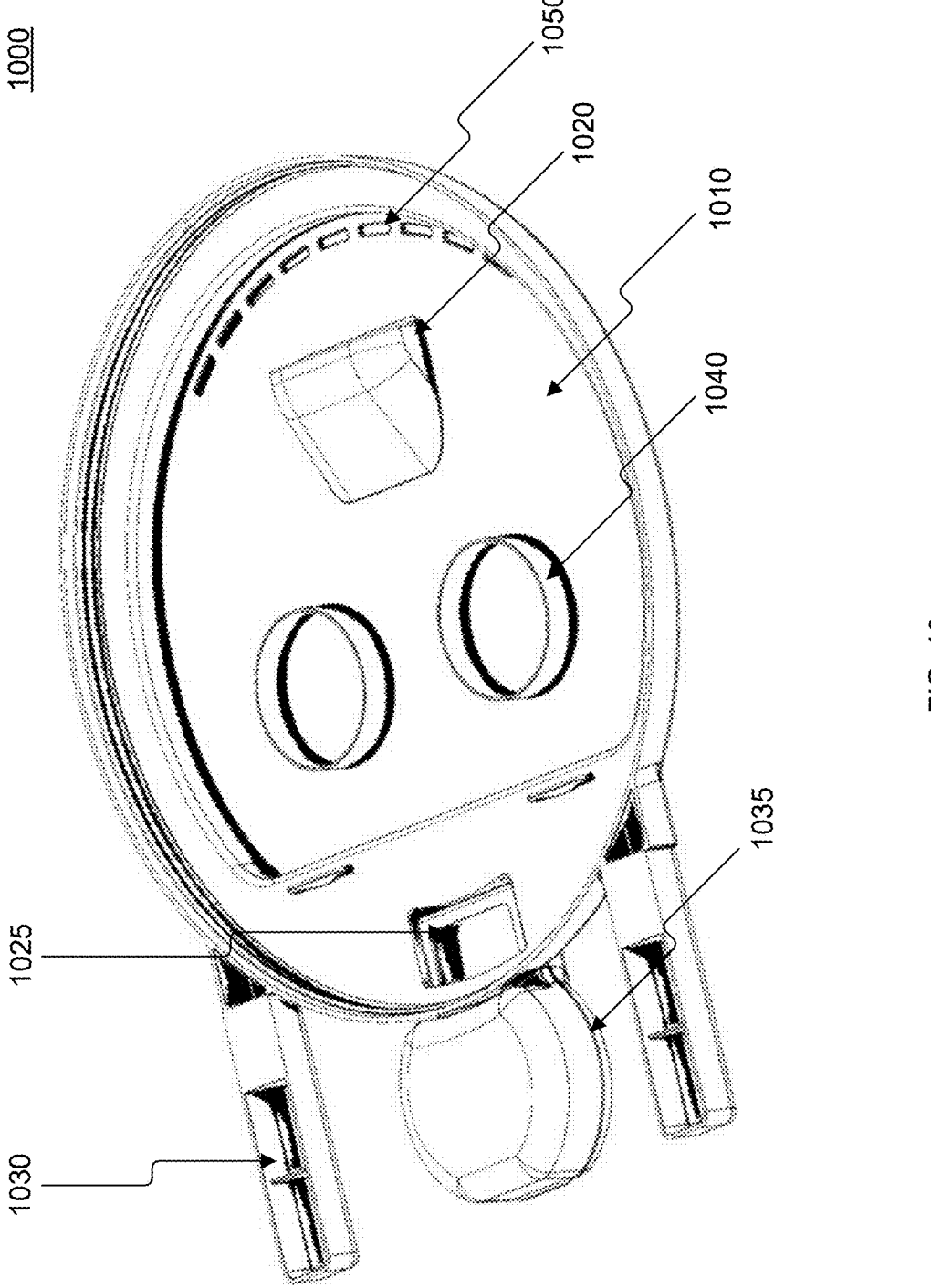
FIG. 10 illustrates a bottom view of a breeder device, according to some embodiments of the present disclosure. The Figures are not necessarily drawn to scale, as their dimensions can be varied considerably without departing from the scope of the present disclosure.

Referring now to FIG. 10, a bottom view of a breeder device, according to some embodiments of the present disclosure, is illustrated. In some embodiments, the breeder device 1000 may include a door 1010, a breeder device access point 1020, an attachment mechanism 1030, and one or more breeder device ports 1040. In some aspects, the breeder device 1000 may be connectable to a breeding container, wherein the opening of the door 1010 may provide access to the breeding container. In some aspects, a handle may be configured to provide leverage to open and close the door 1010. In some implementations, the attachment mechanism 1030 may be configured to secure the breeder device 1000 to a breeding container. In some embodiments, the one or more breeder device ports 1040 may be configured to provide an entrance and an exit for flies and their larvae, as non-limiting examples.

In some embodiments, the breeder device 1000 may include one or more breeding platforms 1040 configured to face the inside of the breeding container, wherein the one or more breeding platforms 1040 may be configured as a place for flies to lay their eggs. In some implementations, the breeder vessel may include at least one aperture 1025 that may be configured to provide an exit for larvae from the breeding container, wherein the larvae may be caught by a tray 1035. In some embodiments, the breeder device 1000 may include one or more holes 1050 configured to provide another point of access for flies and to provide some breathability to the breeder device 1000.

CONCLUSION

A number of embodiments of the present disclosure have been described. While this specification contains many specific implementation details, these should not be construed as limitations on the scope of any disclosures or of what may be claimed, but rather as descriptions of features specific to particular embodiments of the present disclosure.

Certain features that are described in this specification in the context of separate embodiments can also be implemented in combination or in a single embodiment. Conversely, 5 various features that are described in the context of a single embodiment can also be implemented in combination in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous.

Moreover, the separation of various system components in the embodiments described above should not be understood as requiring such separation in all embodiments, and it should be understood that the described components and systems can generally be integrated together in a single product or packaged into multiple products.

Thus, particular embodiments of the subject matter have been described. Other embodiments are within the scope of the following claims. In some cases, the actions recited in the claims can be performed in a different order and still achieve desirable results. In addition, the processes depicted in the accompanying figures do not necessarily require the particular order show, or sequential order, to achieve desirable results. In certain implementations, multitasking and parallel processing may be advantageous. Nevertheless, it will be understood that various modifications may be made without departing from the spirit and scope of the claimed disclosure.

Reference in this specification to "one embodiment," "an embodiment," any other phrase mentioning the word "embodiment", "aspect", or "implementation" means that a particular feature, structure, or characteristic described in connection with the embodiment is included in at least one embodiment of the disclosure and also means that any particular feature, structure, or characteristic described in connection with one embodiment can be included in any embodiment or can be omitted or excluded from any embodiment. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others and may be omitted from any embodiment. Furthermore, any 5 particular feature, structure, or characteristic described herein may be optional.

Similarly, various requirements are described which may be requirements for some embodiments but not other embodiments. Where appropriate any of the features discussed herein in relation to one aspect or embodiment of the invention may be applied to another aspect or embodiment of the invention. Similarly, where appropriate any of the features discussed herein in relation to one aspect or embodiment of the invention may be optional with respect to and/or omitted from that aspect or embodiment of the invention or any other aspect or embodiment of the invention discussed or disclosed herein.

The terms used in this specification generally have their ordinary meanings in the art, within the context of the disclosure, and in the specific context where each term is used. Certain terms that are used to describe the disclosure are discussed below, or elsewhere in the specification, to provide additional guidance to the practitioner regarding the description of the disclosure. For convenience, certain terms may be highlighted, for example using italics and/or quotation marks: The use of highlighting has no influence on the scope and meaning of a term; the scope and meaning of a term is the same, in the same context, whether or not it is highlighted.

It will be appreciated that the same thing can be said in more than one way. Consequently, alternative language and synonyms may be used for any one or more of the terms discussed herein. No special significance is to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and is not intended to further limit the scope and meaning of the disclosure or of any exemplified term. Likewise, the disclosure is not limited to various embodiments given in this specification.

Without intent to further limit the scope of the disclosure, examples of instruments, apparatus, methods and their related results according to the embodiments of the present disclosure are given below. Note that titles or subtitles may be used in the examples for convenience of a reader, which in no way should limit the scope of the disclosure. Unless otherwise defined, all technical and scientific terms used herein have the same meaning as commonly understood by one of ordinary skill in the art to which this disclosure pertains. In the case of conflict, the present document, including definitions, will control.

It will be appreciated that terms such as "front," "back," "top," "bottom," "side," "short," "long," "up," "down," "aft," "forward," "inboard," "outboard" and "below" used herein are merely for ease of description and refer to the orientation of the components as shown in the figures. It should be understood that any orientation of the components described herein is within the scope of the present invention.

What is claimed is:

1. A lid including:

a lip attachable to an entrance of a breeding container;

a main body;

a door attached to the main body, wherein the door is configured to open to provide access to the breeding container;

a breeder device access point protruding from both sides of the door, wherein the breeder device access point includes an internal cavity accessible from each side of the lid; and at least one or more stabilizing legs attachable to the entrance of the breeding container.

2. The lid of claim 1, wherein the lid includes a tray attached to main body below the breeder device access point, wherein the tray includes a surface that protrudes horizontally from the lid, wherein the tray is further configured to function as a stabilizing leg for the breeder device.

3. The lid of claim 2, wherein the lid includes at least one aperture, wherein the at least one aperture is positioned above the tray.

4. The lid of claim 1, wherein the breeding container is a 5-gallon bucket.

5. The lid of claim 1, wherein the breeder device access point is L-shaped, wherein one side of the breeder device access point includes an angle.

6. The lid of claim 1, wherein the breeder device access point includes a first opening and a second opening, wherein the second opening is opposite of the first opening.

7. The lid of claim 6, wherein the second opening includes a breeding platform, wherein the breeding platform surrounds the outside surface of the breeder device access point and is configured to provide an area for flies to lay eggs.

8. The lid of claim 7, wherein the breeding platform includes cardboard.

9. The lid of claim 1, wherein the door is connected to a hinge to facilitate opening and closing of the door.

10. The lid of claim 9, wherein the breeding container is a bucket, a trough, a bin, or a barrel.

11. The lid of claim 10, wherein the breeding container is configured to contain breeding material.

12. The lid of claim 1, wherein the lid is configured to provide access to flies through the breeder device access point, wherein the flies enter the breeding container to lay eggs that produce larvae configured to exit the breeding container at a second breeder device access point located on the main body to provide food for poultry.

13. The lid of claim 1, wherein the one or more stabilizing legs are collapsable, and wherein the one or more stabilizing legs are configured to fold one or both inwards and outwards.

14. The lid of claim 1, wherein the breeder device access point includes one or more bellows configured to make the breeder device access point collapsable and capable of movement.

15. A breeding system including:

a breeder device that includes:

a breeding container, wherein the breeding container is configured to receive breeding material;

a lid configured to attach to the breeding container, wherein the lid includes a lip attachable to an entrance of the breeding container, wherein the lid further includes:

a main body;

a door connected to the lid at an opening on the main body, wherein the door opens and closes to provide access to the breeding container; and a breeder device access point protruding from both sides of the door, wherein the breeder device access point includes an internal cavity accessible from each side of the breeder device; and at least one or more stabilizing legs attached to a periphery of the breeding container.

16. The breeding system of claim 15, wherein the breeder device further includes a tray below the breeder device access point.

17. The breeding system of claim 15, wherein the breeder device is configured to receive flies, wherein the flies are drawn to lay eggs within the breeding container, wherein the larvae feed on the breeding material and provide food to poultry.

18. The breeding system of claim 15, wherein the breeder device includes a breeding platform attached to a side of the breeder device access point that protrudes into the breeding container.

19. The breeding system of claim 15, wherein the breeding container includes at least one opening on a side of the breeding container configured to receive the breeding material.

20. A method of breeding larvae including:

attaching a lid to a breeding container, wherein the lid includes a lip attachable to an entrance of the breeding container, wherein the lid further includes:

a main body and a door attached to the main body, wherein the door is configured to open to provide access to the breeding container, a breeder device access point protruding from both sides of the door, wherein the breeder device access point includes an internal cavity accessible from each side of the breeder device, and at least one or more stabilizing legs attachable to the lip of the breeder device;

receiving flies through a breeder device, wherein the flies enter through a breeder device access point to enter a breeding container with breeding material;

providing a breeding platform within the breeding container configured to receive the eggs of the flies;

feeding larvae hatched out of the eggs, wherein the larvae feeds on the breeding material;

converting the breeding material into fertilizer by the larvae and flies as they consume the breeding material; and capturing the larvae with a tray outside of the breeding container, wherein the larvae provides food to poultry.

* * * * *